United States Patent [19]
Oblinger

[11] 4,281,197
[45] Jul. 28, 1981

[54] HYDROLYTIC DECOMPOSITION METHOD

[75] Inventor: Fred G. Oblinger, Livonia, Mich.

[73] Assignee: Ford Motor Company, Dearborn, Mich.

[21] Appl. No.: 194,164

[22] Filed: Oct. 6, 1980

Related U.S. Application Data

[63] Continuation-in-part of Ser. No. 49,511, Jun. 18, 1979, abandoned, which is a continuation of Ser. No. 826,915, Aug. 22, 1977, abandoned.

[51] Int. Cl.$^3$ .................. C07C 85/26; C08J 11/00
[52] U.S. Cl. .................. 564/393; 260/2.3;
521/63; 521/918; 528/44; 528/67; 564/334;
564/377; 564/386; 564/414; 564/437; 568/753;
568/854; 568/858; 568/613; 568/675
[58] Field of Search .................. 564/393, 414, 377;
260/2.3; 521/63; 528/44

[56] References Cited

U.S. PATENT DOCUMENTS

| 3,225,094 | 12/1965 | Wolf | 564/393 |
| 4,025,559 | 5/1977 | Johnson | 564/414 X |
| 4,051,212 | 9/1977 | Grigat et al. | 564/393 X |
| 4,196,148 | 4/1980 | Mahoney | 564/393 X |

FOREIGN PATENT DOCUMENTS 1455454 10/1976 United Kingdom ............ 564/393

OTHER PUBLICATIONS

Perry, "Chemical Engineer's Handbook", 4th Ed., pp. 8-63 & 8-64 (1974).

*Primary Examiner*—John Doll
*Attorney, Agent, or Firm*—Roger L. May; Olin B. Johnson

[57] ABSTRACT

Porous polyurethane solids such as open cell polyurethane foams are rapidly heated and hydrolytically decomposed into separate polyol component and diamine component by contacting the porous solids with saturated steam in a heated vacuum chamber. Separation of high quality liquid polyol and diamine is achieved.

13 Claims, 1 Drawing Figure

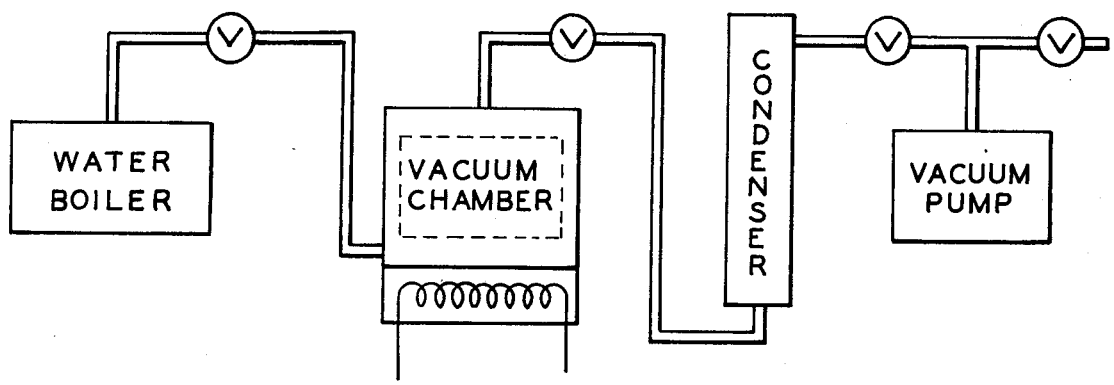

HYDROLYTIC DECOMPOSITION METHOD

This application is a continuation-in part of Ser. No. 049,511 filed June 18, 1979, which is a Continuation of Ser. No. 826,915 filed Aug. 22, 1977 and both now abandoned.

BACKGROUND OF THE INVENTION

The recovery of reactive components from polyurethane scrap material, such as polyurethane foam, has been the subject of considerable inventive effort. Despite this effort, polyurethane foam still is often disposed of commercially in land fill. It is apparent that a need exists for expedient methods and aparatus for processing such materials so as to recover reuseable reactants including polyol and diamine and avoid the necessity for alternative disposal techniques.

Among the approaches proposed for recovery, hydrolysis is known to offer certain advantages, particularly if it can eliminate or reduce a need for larg scale use of organic solvents. The low thermal conductivity of materials such as polyurethanes, however, normally is a limitation in gaseous hydrolysis methods due to extended warm-up periods required before conditions satisfactory for hydrolysis are obained. Such warm-up periods are troublesome even though catalysts may speed the decomposition reaction after hydrolytic decomposition conditions are attained.

Another difficulty encountered with known hydrolytic decomposition methods is that of contamination of recovered polyol with water and amine. Seemingly low levels of water and amine in recovered polyol can markedly reduce the value of the polyol. The value of the polyol, understandably, is integral factor for determining competitiveness of the hydrolytic process.

The invention overcomes the aforementioned deficiencies of prior art hydrolytic recovery processes by providing a hydrolytic decomposition process which allows rapid heating of porous polyurethane foams, such as open cell polyurethane foams and like materials, and separation of high quality polyol and diamines therefrom.

BRIEF DESCRIPTION OF THE INVENTION

The invention is an improvement of processes for hydrolytically decomposing porous polyurethane solids disposed in a chamber and separating liquid polyol therefrom. The improved process comprises:

(A) evacuating the chamber in which the porous polyurethane solids are disposed to a pressure below about $10^{-1}$ atmospheres;

(B) preheating the chamber walls and thereafter admitting saturated steam into said chamber to provide at least 30 atmospheres of presure therein;

(C) maintaing a temperature in the chamber sufficient to continue hydrolytic decomposition and to promote separation of gaseous diamine and liquid polyol in the chamber;

(D) exhausting gaseous effluent from the upper portion of the chamber;

(E) cooling the chamber; and (F) collecting liquid polyol from the lower portion of the chamber.

BRIEF DESCRIPTION OF THE DRAWING

The drawing shows in schematic relationship the various components of apparatus suitable to carry out the process of this invention.

DETAILED DESCRIPTION OF THE INVENTION

Referring to the drawing, the general steps of the process of the invention will be discussed in greater detail.

As indicated above, the process of the invention is a process of hydrolytically decomposing porous polyurethane solids which are disposed in a chamber. The porous polyurethane solids are first introduced into the vacuum chamber shown on the drawing.

The expression "porous polyurethane solids" is intended to include not only open pore polyurethane foam, particularly flexible open pore polyurethane foam, but also polyurethane foam which has been comminuted, thereby providing porosity to the body of the polyurethane solids disposed in the vacuum chamber. Comminution of solids is particularly suitable for those cases wherein the polyurethane solids to be hydrolytically decomposed are of the closed pore variety. However, such comminuted solids could alos be polyurethane foams of open pore type. It will be appreciated that the porosity of polyurethane solids affords exposure of a large surface area of the material to be decomposed to the water vapor which is introduced into the vacuum chamber. The foam, whether of the open or closed pore variety and whether in blocks or comminuted, may be disposed preferably within the chamber in a perforated container such as a perforated metal basket.

In those instances where the process is employed in the decomposition of open pore polyurethane foam of the flexible variety, it is possible to introduce greater amounts of the open pore foam into the vacuum chamber by compressing the foam therein. It has been found practical, depending of course upon the flexibility and the porosity of the foam, to compress the foam to 1/5 or less of its original volumn.

After the foam to be hydrolytically decomposed is disposed within the vacuum chamber, the chamber is evacuated to remove residual air to a pressure below about $10^{-1}$ atmospheres, preferably below about $3 \times 10^{-2}$ atmospheres. As will be noted from the drawing, the chamber is evacuated by using a conventional vacuum pump.

The walls of the vacuum chamber are preheated either subsequent to or during the period in which the vacuum chamber is being evacuated. This preheating is effected by using conventional wall heaters and controls which are shown schematically in the drawing. The chamber may be preheated at this point in the process to the temperature or near the temperature at which the hydrolytic decomposition process is carried out. Alternatively, it may be preheated to a temperature below the ultimately desired temperature and the process carried out such that the heating is continued during subsequent steps until the ultimately desired temperature is achieved. The desired temperatures will be discussed more fully hereinafter.

After the chamber walls are preheated at least in part, high pressure saturated steam (water vapor) is introduced into the vacuum chamber to provide a pressure therein of at least about 30 atmospheres or greater.

Heating of the walls continues during this stage, if the desired temperature has not already been achieved. The temperature of the walls most desirably reaches a range that prevents substantial condensation of water vapor thereon (e.g., 200° C. or higher). After introduction of the saturated steam, the temperature in the chamber is maintained sufficiently high to continue hydrolytic decomposition and to promote separation of gaseous diamine and liquid polyol in the vacuum chamber. The chamber is maintained at this temperature by maintaining the temperature of the walls sufficiently high, preferably at a temperature corresponding to about the steam saturation temperature at the selected operating pressure in the vacuum chamber. As noted above, a temperature of 200° C. or higher for the chamber walls is desirable. As also noted above, the temperature at which the chamber is maintained may be achieved during the preheating stage of the process or, alternatively, may be achieved during the subsequent processing steps after or during introduction of the saturated steam into the vacuum chamber.

Heating of the porous polyurethane solids to hydrolytic decomposition conditions occurs rapidly (i.e., within about 10 minutes or less, desirably in as little as about 1-3 minutes) because it reaches a temperature corresponding to the vapor pressure of steam admitted to the vacuum chamber nearly instantaneously. This is particularly so when the chamber has been preheated to the ultimately desired temperature for the hydrolytic decomposition. Rapid attainment of temperature is achieved even in those instances where porous polyurethane solids, such as open pore flexible polyurethane foam, is initially compressed to less than 1/5 its original volumn in the vacuum chamber.

The boiler, depicted schematically in the drawing, may be any standard type boiler that provides saturated steam at pressures at least greater than about 30 atmospheres, more preferably greater than 35 atmospheres or more and up to even higher pressures provided the system can conveniently handle them. Normally, pressures between about 35-60 atmospheres can be employed in the vacuum chamber to give advantageous results without resort to more costly high pressure equipment.

Upon hydrolytic decomposition of the porous polyurethane solids, gaseous effluent is exhausted from the upper portion of the vacuum chamber and cooled in a condenser wherein water and liquid or solid diamines are collected. A release of carbon dioxide also occurs and such gas can be vented from the consenser. Advantageously, the cooling condenser may comprise a plurality of small metallic pieces to insure maximum surface area for collection of diamine component.

Usually a period of about 30 minutes is required for complete hydrolytic decomposition of polyurethane foam at saturated vapor pressures of about 30-40 atmosphere, although action of catalysts as well as higher pressures may reduce the time required. Continuance of admission of the saturated steam to maintain such pressures permits the endothermic reaction to proceed expeditiously.

After hydrolytic decomposition is completed, introduction of saturated steam is discontinued and the vacuum chamber cooled prior to collecting the liquid polyol from the lower portion of the chamber.

It is desirable, prior to cooling and removal of the polyol product from the bottom of the chamber, to continue evacuation of the vacuum chamber, after completion of hydrolytic decomposition, to pressures below about $10^{-1}$ atmospheres and more preferably below about $2 \times 10^{-2}$ atmospheres in order to dry and purify the liquid polyol residue in the bottom of the vacuum chamber. In this way, the liquid polyol decomposition component may conveniently be freed of excess water and diamines, thereby increasing the value of this component. After sufficient water and excess diamine have distilled off, the vacuum may then be released, the vacuum chamber cooled and the liquid component collected. Ideally, the pressure in the vacuum chamber is maintained at $2 \times 10^{-2}$ atmospheres while maintaining the wall temperature of the chamber at about 271° C. for about 20 minutes to remove the residual water and amines from the polyol in the chamber. The process may then, of course, be begun again by once again introducing porous polyurethane solids into the vacuum chamber from a standby holding chamber.

The following examples illustrates this invention and are not intended as limited the scope thereof, as many modifications will be apparent according to the hereinbefore and hereinafter descriptions of this invention.

EXAMPLE 1

Using an apparatus as illustrated in the drawing, urethane foam, at a density of 48 kg/m$^3$ is stuffed into the reactor (i.e., vacuum chamber) and compressed to about 240 kg/m$^3$. The reactor is sealed and the vacuum pump started. The reactor with its exhaust system, including condensers, is evacuated to an absolute pressure of approximately 2 kPa (15 mm Hg or 0.3 psia). The high pressure boiler is energized and brought up to pressure, about 10,300 kPa at 315° C. The reactor exhaust valve is closed—vacuum pump operation continues—and the electric heaters on the reactor sidewalls and in the reactor base and top flange are energized, with the heater controls set at the desired wall temperature (200° to 250° C.). Steam is immediately admitted to the reactor until a reactor pressure of 3.8 MPa to 4.1 MPa (550 psig to 600 psig) is attained. As soon as this pressure is reached, a 250° to 255° C. temperature is immediately established within the reactor. Steam flow rate is then reduced until reactor pressure is just maintained for a period of not more than 30 minutes, when the reactions will have been well completed. The steam valve is then closed and the reactor exhaust valve is partially opened. The exhaust valve is modulated so as not to exceed a pressure of 6.5 kPa absolute (0.9 psia) in the vacuum system. This prevents an excessive flow of vapor into the vacuum pump. After the reactor pressure has again been reduced to 2 kPa absolute (0.3 psia) at a reactor temperature of about 271° C., and the pressure and temperature maintained for about 20 minutes, the reactor heaters are de-energized and the reactor is cooled to room temperature. After venting to the atmosphere, the polyol is draind from the reactor for use. (The polyol has less than ¼% by weight amine and less than ¼% by weight water). The toluene diamine is removed from the condenser system by heating and draining, re-evaporating, or with a solvent flush. The residue, composed of fillers such as crushed dolomite, poly propylene, etc. is removed from the reactor and the equipment is then ready for re-use.

EXAMPLE 2

Urethane foam, at a density of 36.8 Kg/m$^3$ is stuffed or packed into a basket constructed from perforated stainless steel sheet and compressed to a density of 500 kg/m³. The basket with its contents is then placed in the reactor. The reactor is sealed and the procedure of Example 1 is followed leading to similar diamine and polyol separation.

EXAMPLE 3

Non-porous urethane is reduced to small chips of less than 1 mm in any dimension which are placed in a perforated metal or metal mesh basket. The basket, loaded with urethane chips is placed in the reactor. The reactor is sealed, whereupon the procedure of Example 1 is followed leading to desired polyol and diamine components.

It is to be understood that the apparatus as shown in the drawing may be advantageously modified such that the boiler surrounds the vacuum chamber thereby eliminating the need for separate heating element to heat the vacuum chamber. On the other hand, the apparatus as shown permits ready construction and has the advantage that the exterior of the vacuum chamber may be heated to some extent by the entering saturated steam condensing on the inner walls thereof thereby preventing undesirably high temperature walls contacting porous solids in the absence of saturated water vapor. Still further, the apparatus as illustrated in the drawing advantageously allows for precise control of reaction conditions so that high quality decomposition products may be consistently obtained.

In view of this disclosure, many modifications of this invention will be apparent to those skilled in the art. It is intended that all such modifications which fall within the true scope of the invention be included within the terms of the appended claims.

What is claimed is:

1. In a process for hydrolytically decomposing porous polyurethane solids disposed in a chamber and separating liquid polyol therefrom the improvement comprising:
   (A) evacuating said chamber to a pressure below about $10^{-1}$ atmospheres;
   (B) preheating the walls of said chamber and thereafter admitting saturated steam into said chamber to provide at least about 30 atmospheres of pressure therein;
   (C) maintaining a temperature in said chamber sufficient to continue hydrolytic decomposition and to promote separation of gaseous diamine and liquid polyol in said chamber;
   (D) exhausting gaseous effluent from the upper portion of said chamber;
   (E) cooling said chamber; and
   (F) collecting liquid polyol from the lower portion of said chamber.

2. A process in accordance with claim 1, wherein said chamber is evacuated to a pressure below $3 \times 10^{-2}$ atmospheres.

3. A process in accordance with claims 1 or 2, wherein said temperature in said chamber is maintained at a temperature sufficient to continue hydrolytic decomposition and to promote separation in said chamber of gaseous diamine and liquid polyol by maintaining the temperature of the walls of said chamber at a temperature corresponding to about the steam saturation temperature at the selected operating pressure in said chamber.

4. A process in accordance with claim 3, wherein said walls of said chamber are maintained at a temperature of about 200° C. or higher.

5. A process in accordance with claim 1, wherein said chamber is evacuated subsequent to hydrolytic decomposition of said porous polyurethane solids to remove diamine and water therefrom.

6. A process in accordance with claim 5, wherein subsequent to hydrolytic decomposition said chamber is evacuated to a pressure below $10^{-1}$ atmosphere and said walls of said chamber are maintained at a temperature above about 200° C. for a time necessary to distill amine from residual polyol in said chamber.

7. A process in accordance with claim 5, wherein subsequent to hydrolytic decomposition said chamber is evacuated to a pressure below $2 \times 10^{-2}$ atmospheres and said walls of said chamber are maintained at a temperature of about 271° C. for about 20 minutes.

8. A process in accordance with claim 1, wherein said porous polyurethane solids comprise open pore polyurethane foam.

9. A process in accordance with claim 8, wherein said foam is compressed to less than 1/5 its original volume.

10. A process in accordance with claim 1, wherein said porous polyurethane solids comprise comminuted closed pore polyurethane foam.

11. A process in accordance with claim 1, 8, or 10, wherein said porous polyurethane solids in said chamber are disposed in a perforated container.

12. A process in accordance with claim 1 or 5, wherein said walls of said chamber are preheated to a temperature corresponding to about the steam saturation temperature at the pressure at which said chamber is to be maintained during hydrolytic decomposition of said porous polyurethane foam.

13. A process in accordance with claim 12, wherein said walls of said chamber are preheated to a temperature above about 200° C.

* * * * *